United States Patent [19]
Lanotte

[11] Patent Number: 5,712,894
[45] Date of Patent: Jan. 27, 1998

[54] STERILIZATION CELL

[76] Inventor: Michel Lanotte, 12 Chemin des Meules, Jons, France, 69330

[21] Appl. No.: 556,545

[22] Filed: Nov. 28, 1995

[30] Foreign Application Priority Data

Nov. 30, 1994 [FR] France ............... 94 14611

[51] Int. Cl.⁶ .................................................. G21K 5/08
[52] U.S. Cl. .......................... 378/68; 378/64; 378/69
[58] Field of Search ............................. 378/64, 68, 69, 378/66, 67, 195, 196, 208

[56] References Cited

U.S. PATENT DOCUMENTS

| 3,484,612 | 12/1969 | Kuenzli | 378/68 |
| 4,481,652 | 11/1984 | Ransohoff | 378/69 |
| 4,788,701 | 11/1988 | Barrett | 378/68 X |
| 5,001,352 | 3/1991 | Tetzlaff | 378/69 X |

*Primary Examiner*—David P. Porta
*Attorney, Agent, or Firm*—Dowell & Dowell

[57] ABSTRACT

A gamma radiation cell for sterilizing industrial products, of the type constituted by a shielded enclosure provided with at least one tight access door, comprising an overhead conveyor for displacing transports supporting the products to be treated. The floor of the enclosure comprises a central well allowing storage of a source of irradiation which may be moved vertically. Pipes connect this well to an oxygen reserve and to a reservoir for storing the ozone produced by radiolysis, this ozone being able to be admitted into the vessel of the transports.

10 Claims, 4 Drawing Sheets

STERILIZATION CELL

BACKGROUND OF THE INVENTION

1. Field of the Invention

The present invention relates to a sterilization cell for industrial products, which makes good use of the effects, well known per se, of energy of the gamma radiation on the inter atomic bonds of the RNA and DNA chains, thus creating the desired conditions of sterility on microbial or microbiological populations.

2. History of the Related Art

Although such a cell is capable of being used for the treatment of all industrial products whatever their nature, the studies and tests made by Applicants have revealed a particular interest for the sterilization of various medical products, particularly in a hospital environment.

SUMMARY OF THE INVENTION

The cell according to the invention, of the type constituted by an entirely shielded enclosure provided with at least one tight access door, itself shielded, is characterized in that it comprises, in combination:

a central well made in its flooring in order to form dry storage for a source of irradiation;

a lifting mechanism for vertical movement of the source of irradiation which may thus take an upper work position and a lower storage position;

a circuit for producing ozone by radiolysis of a stream of oxygen, associated with the central well, which circuit, used when the source is in the lower storage position, connects this well to a reserve of oxygen and to an ozone storing reservoir;

a carrousel constituted by a series of boats or transports intended to receive the products to be sterilized and by a conveyor adapted to displace the transports boats within the cell;

connecting means for connecting the interior space of the vessel of the transports to the ozone-storage reservoir and to an evacuation system;

and insufflation and aspiration means for adequately treating the internal atmosphere of the cell.

It is readily appreciated that such a cell, operating in entirely autonomous manner, makes it possible to adapt the sterilization treatment precisely to the exact nature of the products concerned.

BRIEF DESCRIPTION OF THE DRAWINGS

The invention will be more readily understood on reading the following description with reference to the accompanying drawings, in which.

DESCRIPTION OF PREFERRED EMBODIMENT

Figure 1:
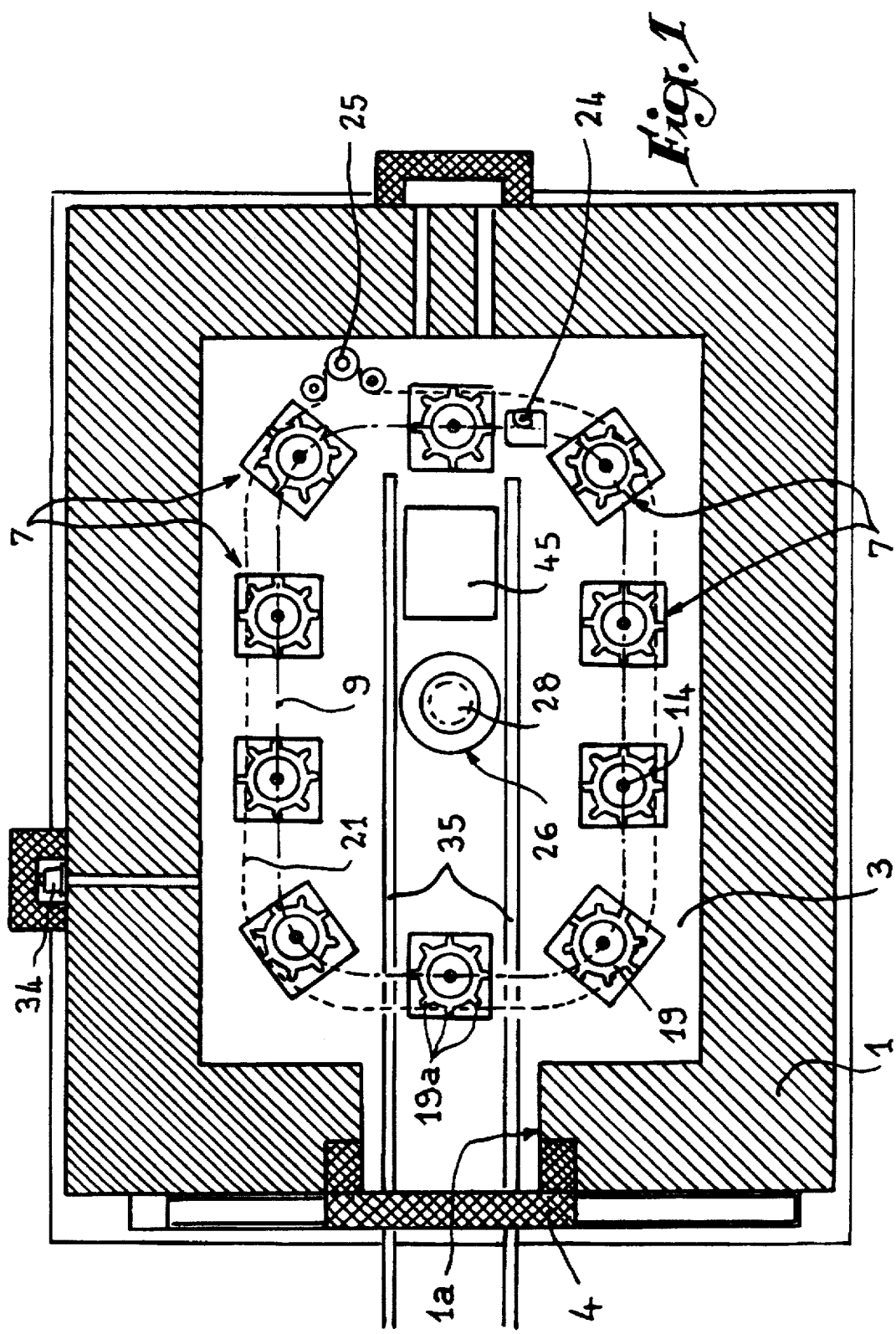
FIG. 1 is a horizontal section showing very schematically the general arrangement of a sterilization cell according to the invention.
Figure 2:
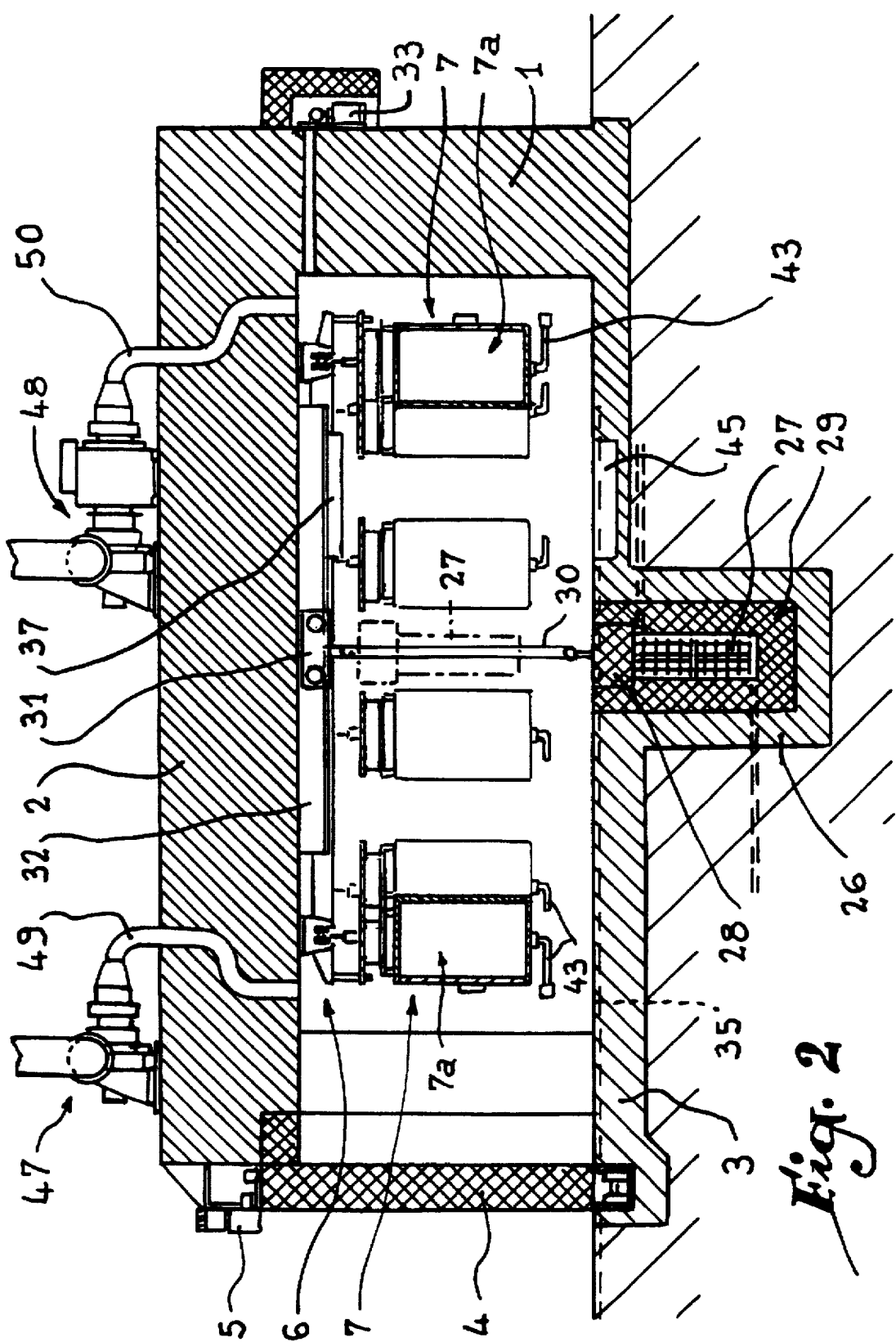
FIG. 2 is the corresponding vertical section thereof.

Referring now to the drawings, the cell shown in FIGS. 1 and 2 essentially comprises a box formed by a lateral wall 1 of rectangular section, a ceiling 2 and floor 3, these three elements 1, 2 and 3 being constituted by shields adapted to ensure an effective biological protection of the environment. The lateral wall 1 is provided with an opening 1 a equipped with a tightly fitted shielded door 4 displaced with the aid of a drive mechanism 5.

Figure 3:
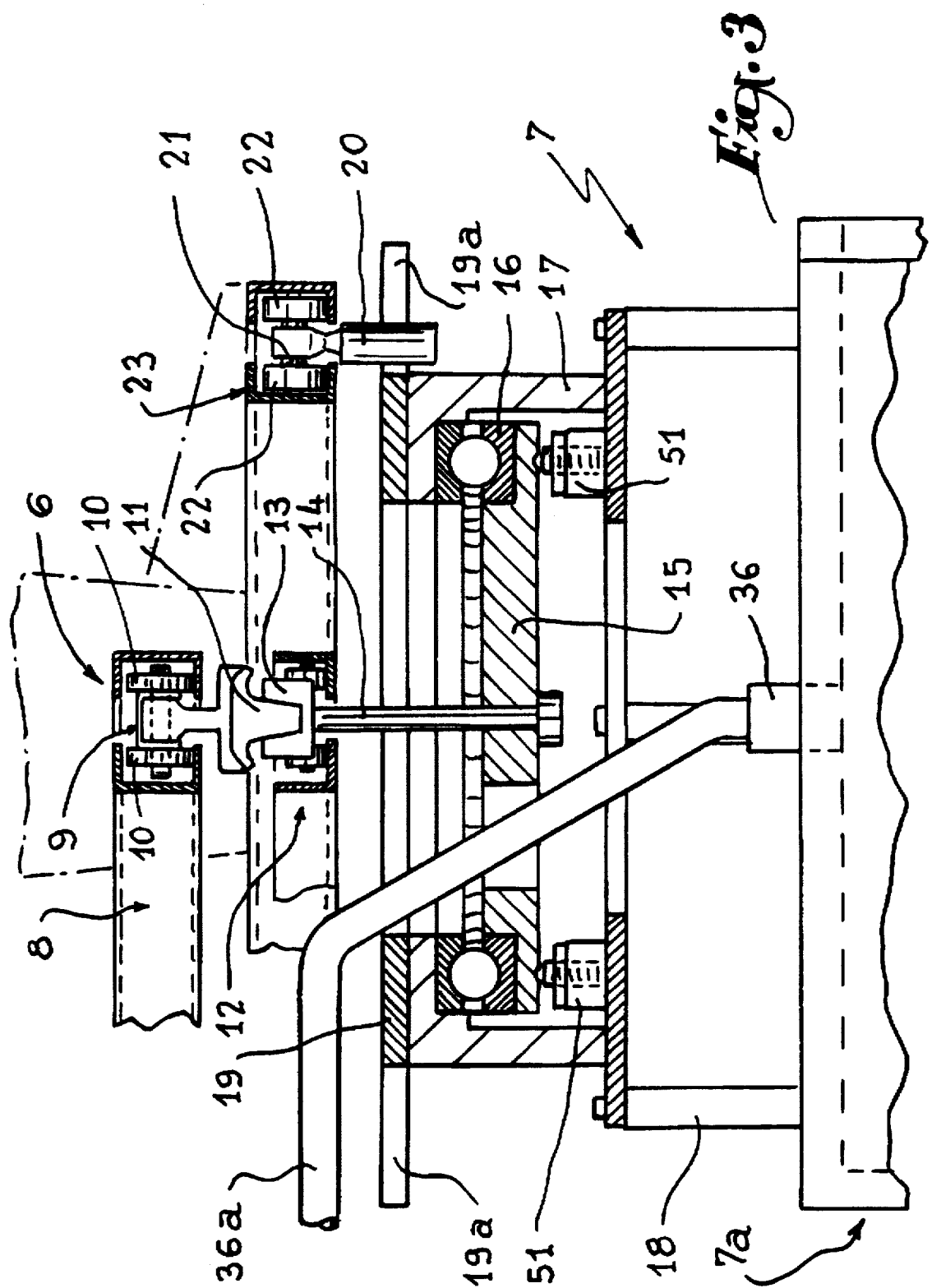
FIG. 3 is a vertical section on a larger scale illustrating the suspension and drive of one of the transports of the carrousel.

The ceiling 2 supports a carrousel which comprises an overhead conveyor 6 for the suspension and displacement of transports 7, ten in number in the embodiment considered. As shown in FIG. 3, the conveyor 6 itself comprises an upper rail 8 inside which moves a chain 9 supported in places by rollers 10; at the level of each pair of rollers 10, the chain 9 is provided with a downwardly facing drive catch 11.

Below the rail 8 and presenting the same profile in plan, there is provided a lower rail 12 inside which move ten carriages 13, each of them being displaced with the aid of one of the catches 11 of the chain 9. Each carriage 13 is secured to a downwardly facing vertical pin 14 for supporting one of the boats 7.

To that end, the base of each pin 14 is rigidly secured to a fixed plate 15 which, via a ball bearing 16, supports a rotating bush 17 secured with the upper part of one of the transports 7 by a cage 18.

It should be observed that, against the upper edge of the bush 17 is fixed a disc 19 of which the periphery, provided to project with respect to the bush, has radial notches cut therein, which define fingers 19a, eight in number in the embodiment shown. As will be set forth hereinafter, these fingers 19a are adapted to cooperate with catches 20 carried by a chain 21, which is supported in places by rollers 22 moving in a fixed rail or sheath 23. This latter extends parallel to the superposed rails 8 and 12, being disposed outwardly with respect thereto.

The chain 9, enclosed by the upper rail 8, is driven in translation by a gear motor 24 (FIG. 1), while the chain 21 mounted in the lateral sheath 23, cooperates, for its drive, with an independent gear motor 25. The two gear motors 24 and 25 are fixed against the ceiling 2.

A well 26 is arranged in the central part of the flooring 3 of the cell. Inside this well 26 is housed a source of irradiation 27 constituted, in manner known per se, by a basket inside which are concentrically mounted pencils of radioactive cobalt (cobalt 60) or other source of gamma radiation. The basket of the source 27 is suspended from a stopper 28 (FIG. 2) forming a lid for the inner vessel 29 of the central well 26, the assembly thus being adapted to define a dry storage.

With the stopper or lid 28, there is associated a block and tackle of which the cable 30 is returned on a carriage 31 which moves on an upper rail 32 fixed against the ceiling 2 of the cell. This cable 30 is controlled by a winch 33 mounted laterally outside the wall 1, while the carriage 31 may be displaced horizontally along the rail 32 by a winch 34. Appropriate means (not shown) are provided to ensure guiding of the assembly 27–28 during its vertical displacements.

On the flooring 3 of the cell are fixed rails 35 for the displacement of a self-propelled carriage (not shown) which carries a manipulator robot intended, in liaison with the winches 33 and 34, to allow initial positioning of the source of irradiation 27 and its replacement when it is spent.

The upper part of at least some of the transports 7 is provided with a rotating joint 36 (FIG. 3) which opens in a vessel 7a fixed to the cage 18 of the boats shown and on which is fastened a radial pipe 36a whose free end, provided with a flap-valve connection, is capable of being connected on one of the flexible pipes of a connection device 37. This latter, fixed against the ceiling 2 of the cell, is connected to atmosphere through appropriate filters.

Figure 4:
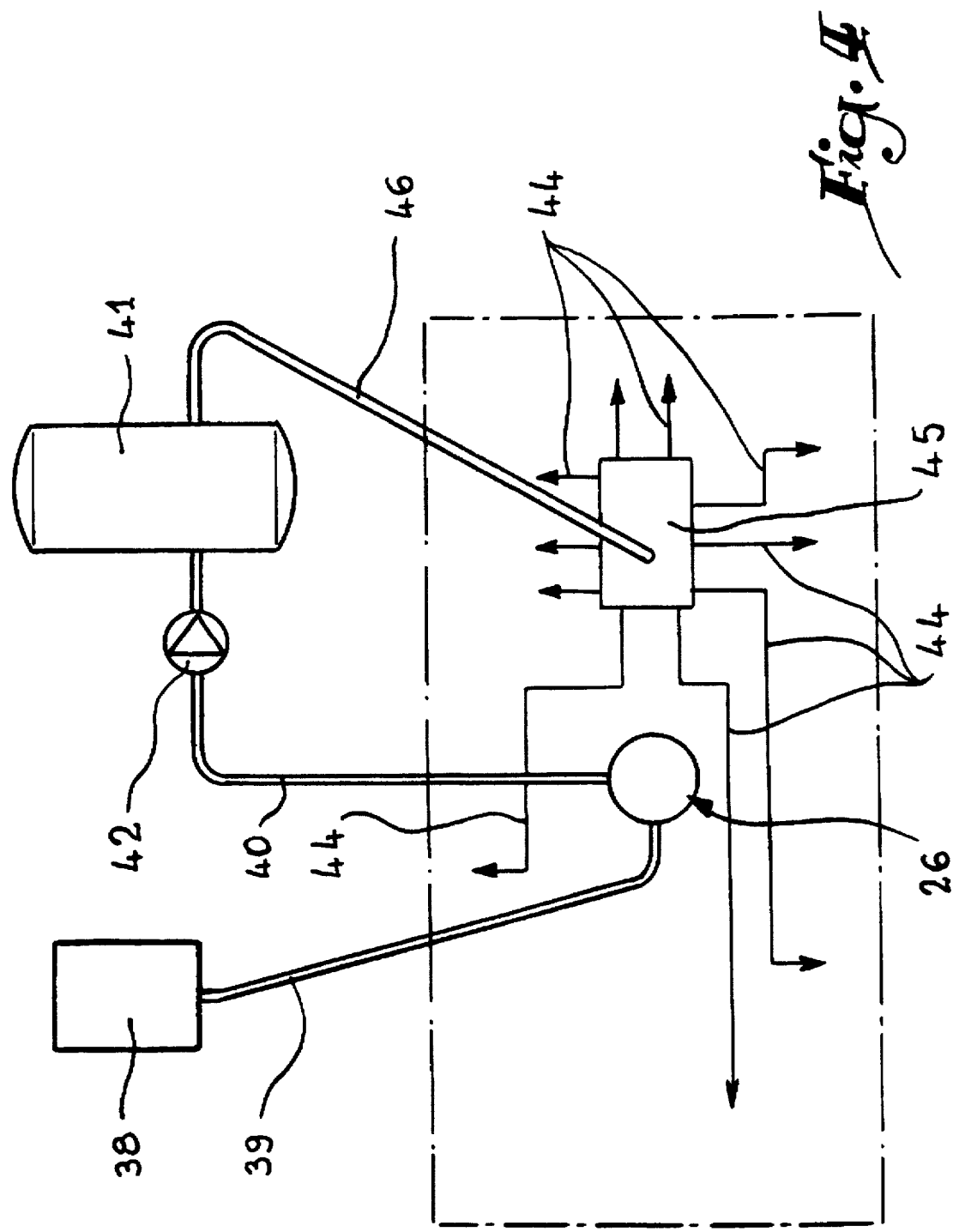
FIG. 4 is a diagram of the circuit for producing ozone and for filling the transports.

The cell is provided with a circuit for producing ozone by radiolysis which comprises a source of oxygen 38 (FIG. 4) placed in communication via a pipe 39 with the base of the vessel 29 of the central well 26 when the source of irradiation 27 is in a lower storage position inside the vessel 29. This latter is connected by an upper pipe 40 to an ozone storage reservoir 41 through a compressor 42.

The base of the vessel 7a of the transports 7 comprises at its center a rotating joint associated with a radial pipe 43 (FIG. 2). Each pipe 43 may be connected by a flexible pipe (shown in the diagram of FIG. 4 in the form of simple arrows referenced 44) to a connection device 45 housed in the flooring 3 of the cell; this device 45 communicates by a pipe 46 with the storage reservoir 41.

The cell according to the invention is further equipped with two motor-driven ventilator units 47 and 48 fixed on the ceiling 2 and equipped with adequate filtration systems. Unit 47 sucks, via a conduit 49, the air or gas which is insufflated into the atmosphere of the cell via a conduit 50 connected to an appropriate source through unit 48; it is on this extraction conduit 49 that the connection provided between the connection device 37 and the atmosphere arrives. Units 47 and 48 are servo-controlled so that a slight depression prevails in the cell.

It goes without saying that the vessel 7a of each transport 7 is equipped with a door ensuring hermetic closure; this vessel 7a comprises supports and other arrangements adapted to allow rational suspension and stowing of the products to be sterilized. As the case may be, the operations of loading and unloading the transports 7 may be effected either inside or outside the cell, the conveyor 6 being, in the latter case, provided with suitable switches.

Whatever the mode of loading, it will be appreciated that, once the products to be sterilized are installed in the vessel 7a of the transports 7, said products are capable of receiving the treatment best suited to their nature and to their state, due to the remarkable operational versatility of the cell according to the present invention. In particular, it will be observed:

that, with the aid of the motor-driven ventilator units 47 and 48 and of conduits 49 and 50, the interior space of the enclosure 1-2-3 may be filled with a gas adapted to promote sterilization (which may, moreover, be ozone directly taken from the well 26), the free ends of the pipes 36a and 43 being, of course, maintained open, as well as the doors of the vessels 7a;

that, on the contrary, the interior space of the vessel 7a of each transport 7 may be filled with ozone or other gas through pipes 43 and 36a mentioned above, by means of the connection devices 45 and 37;

that, by means of the winch 33, the source 27 may be extracted from the central well 26 for irradiation of the content of the vessels of the transports 7, which obviously has for its effect to stop production of ozone inside the vessel 29;

that, by operating gear motor 25 only, boats 7 may be driven in rotation about their support pin 14 while being immobilized in translation, the catches 20 carried by the chain 21 cooperating with the fingers 19a of the disc 19 to rotate each transport;

that, by operating gear motor 24 only, it is possible to displace in translation all the boats 7 in the cell, by rotating them on themselves further to the immobilization of the lateral chain 21 and the catches 20;

and that, if both gear motors 24 and 25 are operated, transports 7 move in translation without rotating on themselves.

It will be noted that, when boats 7 are driven in rotation about their axis, it is advantageous to impart thereto a perfectly regular step-by-step movement. This result may be obtained with the aid of elastic ball-bearing positioners 51 (FIG. 3) carried by the cage 18 and adapted to cooperate with impressions made in the lower face of the corresponding fixed plate 15.

It should be observed that spray nozzle pipes or nozzles may be disposed inside the cell, arranged to allow admission of a stream of oxygen during the treatment (source 27 in upper work position) in order to be recovered in the form of ozone either for storage or for another direct use outside. Furthermore, transports 7 may be driven in rotation about their axis with the aid of independent motors, of the step-by-step type.

It will also be understood that the source of irradiation 27 may be moved vertically with the aid of a pneumatic or hydraulic jack acting as a central shaft, in place of the lifting cable system 30–33 described hereinbefore.

The central well 26 and the vessel 29 that it contains may be provided to be dismountable in order to be able to be manipulated and used in the manner of a packaging for transporting the source.

What is claimed is:

1. A gamma radiation cell for sterilizing products and including a shielded enclosure provided with at least one access door, wherein the cell comprises in combination:

a central well in a floor of the enclosure adapted to form a dry storage area for a source of irradiation;

a lifting mechanism adapted to vertically move the source of radiation between an upper work position and a lower storage position;

a fluid circuit connecting said central well to a reserve of oxygen and to an ozone storing reservoir for producing ozone by radiolysis of a stream of oxygen when the source of irradiation is in the lower storage position;

a conveyor including a series of transports adapted to receive the products to be sterilized and means for moving said conveyor to displace said transports within an internal space of the enclosure;

connecting means for connecting an interior space of each of said transports to said ozone storing reservoir and to an evacuation system; and insufflation and aspiration means for adjusting pressure within said internal space of the enclosure.

2. The cell of claim 1 wherein each transport is rotatably mounted about a vertical pin which connects each transport to said conveyor.

3. The cell of claim 2 including a roller bearing interposed between an upper part of each transport and a fixed plate carried by each of said pins, a notched disk secured to each of said upper parts, and a chain disposed adjacent to said conveyor and including a plurality of catches extending therefrom and engageable with said notched disks.

4. The cell of claim 3 including a motor means for driving said chain independently of said conveyor.

5. The cell of claim 4 wherein a plurality of said transports include a vessel having a door.

6. The cell of claim 5 wherein said connecting means for communicating said interior space of each transport includes rotatable joints.

7. The cell of claim 6 wherein said insufflation and aspiration means includes two motor-driven ventilators.

8. The cell of claim 1 wherein a plurality of said transports include a vessel having a door.

9. The cell of claim 1 wherein said insufflation and aspiration means includes two motor-driven ventilators.

10. The cell of claim 1 wherein said connecting means for communicating said interior space of each transport includes rotatable joints.

* * * * *